United States Patent
Sven-Erik et al.

(10) Patent No.: US 8,133,186 B2
(45) Date of Patent: Mar. 13, 2012

(54) IMPLANTABLE SENSOR LEAD

(75) Inventors: Hedberg Sven-Erik, Kungsängen (SE);
Per Lagercrantz, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 607 days.

(21) Appl. No.: 12/160,666

(22) PCT Filed: Jan. 12, 2006

(86) PCT No.: PCT/SE2006/000046
§ 371 (c)(1),
(2), (4) Date: May 13, 2009

(87) PCT Pub. No.: WO2007/081246
PCT Pub. Date: Jul. 19, 2007

(65) Prior Publication Data
US 2009/0253993 A1    Oct. 8, 2009

(51) Int. Cl.
*A61B 5/02* (2006.01)
(52) U.S. Cl. ........................................................ 600/508
(58) Field of Classification Search ................. 600/508, 600/425
See application file for complete search history.

(56) References Cited

U.S. PATENT DOCUMENTS

| | | |
|---|---|---|
| 5,243,883 A | 6/1995 | Helland |
| 5,593,430 A | 1/1997 | Renger |
| 5,628,777 A | 5/1997 | Moberg et al. |
| 5,999,848 A | 12/1999 | Gord et al. |
| 2003/0199957 A1 | 10/2003 | Struble et al. |
| 2005/0090870 A1 | 4/2005 | Hine et al. |
| 2008/0183072 A1* | 7/2008 | Robertson et al. ............ 600/425 |

FOREIGN PATENT DOCUMENTS

| | | |
|---|---|---|
| EP | 0 473 040 | 11/1995 |
| EP | 0 727 242 | 8/1996 |
| WO | WO 95/03086 | 2/1995 |

* cited by examiner

*Primary Examiner* — George Manuel
*Assistant Examiner* — Robert Wieland
(74) *Attorney, Agent, or Firm* — Schiff Hardin LLP

(57) ABSTRACT

In an implantable sensor lead for sensing mechanical cardiac activity of a heart, as well as a sensing method and a cardiac stimulator embodying such a sensor lead, multiple cardiac activity sensing elements are distributed along a portion of a length of the lead body of the implantable lead. The sensing elements sense or detect mechanical cardiac activity and respectively emit electrical signals corresponding to the detected mechanical cardiac activity. The delivery of cardiac stimulation pulses can be controlled dependent on an analysis of the detected mechanical cardiac activity.

23 Claims, 4 Drawing Sheets

IMPLANTABLE SENSOR LEAD

BACKGROUND OF THE INVENTION

1. Field of the Invention

The present invention relates to an implantable sensor lead for sensing mechanical cardiac activity of a person, to an electronic device, an implantable cardiac stimulator as well as a method for sensing mechanical cardiac activity of a person.

2. Description of the Prior Art

Sensor signals can be used for purposes such as optimization of biventricular synchronization or setting the AV-delay in connection with cardiac stimulation, diagnosis of congestive heart failure, etc.

Leads carrying mechanical sensor elements, like accelerometers, pressure sensing elements, strain gauges or tensiometers, often suffer from disturbances caused by local forces acting on the sensor elements. Thus, such a sensor element placed on e.g. the left side of the heart in a coronary vein is heavily influenced by local forces close to the sensor element. Similar problems occur in connection with the use of so-called CMES-sensors, Cardio Mechanical Sensors, placed in the right ventricle, in coronary sinus, in great cardiac vein or in a coronary vein. Moreover, the placement of the sensor element of a cardiac sensor is seldom freely selectable.

Sensing elements having a certain extension are previously known as well as the use of more than one sensing element spread out over a part of the heart.

In EP 0 473 070 a myocardial tensiometer incorporated within an implantable electrotherapy apparatus to measure the contraction of the heart muscle is described. The tensiometric element consists of piezoelectric material or a variable resistivity material, the mechanical stresses to which the tensiometric element is subjected causing the element to produce a voltage or resistivity variation. The tensiometric element is disposed at a location which is subject to bending when the heart contracts. Thus the tensiometric element may be in the form of a strip disposed on a surface of a patch electrode, or a strip or a tube located at the bend of an implantable J-shaped pacing lead.

U.S. Pat. No. 5,423,883 discloses an implantable myocardial lead. At the distal end of the lead a plurality of appendages are disposed. These appendages are intended to embrace the tissue of the heart and will flex forward and backward to move with the tissue of the heart. At least one sensor element, like a piezoelectric crystal or an accelerometer, is secured to an appendage for detecting the heart wall motion.

In WO 95/03086 implantable leads incorporating accelerometer-based cardiac wall sensors are described. The sensed cardiac wall motion is used to discriminate among potentially malignant cardiac arrhythmias. The cardiac wall motion sensor may be incorporated in a flexible epicardial patch electrode or be incorporated in an endocardial lead.

SUMMARY OF THE INVENTION

An object of the present invention is to solve the above discussed problem related to disturbances caused by local forces acting on the sensor element when sensing mechanical cardiac activity.

The above object is achieved in accordance with the principles of the present invention by an implantable sensor lead, and by an implantable medical device embodying such a lead, wherein the lead carries multiple sensing elements arranged along the lead body for sensing mechanical cardiac activity, and emitting electrical signals corresponding to the detected mechanical cardiac activity.

The above object also is achieved in accordance with the present invention by a method for sensing mechanical cardiac activity of a patient, that includes the steps of implanting a lead in a patient that carries multiple mechanical cardiac activity sensors, and sensing mechanical cardiac activity using those sensing elements that are distributed relative to the heart of the patient by virtue of being carried along the length of the implanted lead.

Thus by using a number of sensing elements arranged along an implantable lead body for sensing mechanical cardiac activity and delivering corresponding electric signals according to the invention, the cardiac activity is sensed over a larger part or in a larger volume of the heart. The resulting global signals obtained by such a spread out sensing over a larger part or a larger volume of the heart will normally be in phase, whereas local signals often are more or less unsynchronized.

In a preferred embodiment, from the electrical point of view, the sensing elements are connected in parallel between two conductors common to all sensing elements. With such an embodiment a sensor signal averaging will be obtained. Signals in phase will be added, while signals out of phase will be more or less reduced.

In another embodiment of the invention each sensing element of the plurality of sensing elements is connected to at least one conductor of its own. With such an embodiment it is possible to study the propagation of a mechanical cardiac activity, such as mechanical heart muscle contractions, pressure pulses, blood flow along a vein, by analysis of the pattern of electric signals from the plurality of sensing elements. Thus e.g. the cardiac activity propagation speed can be determined, since the distances along the lead body between the individual sensing elements are known.

DESCRIPTION OF THE PREFERRED EMBODIMENTS

Figure 1:
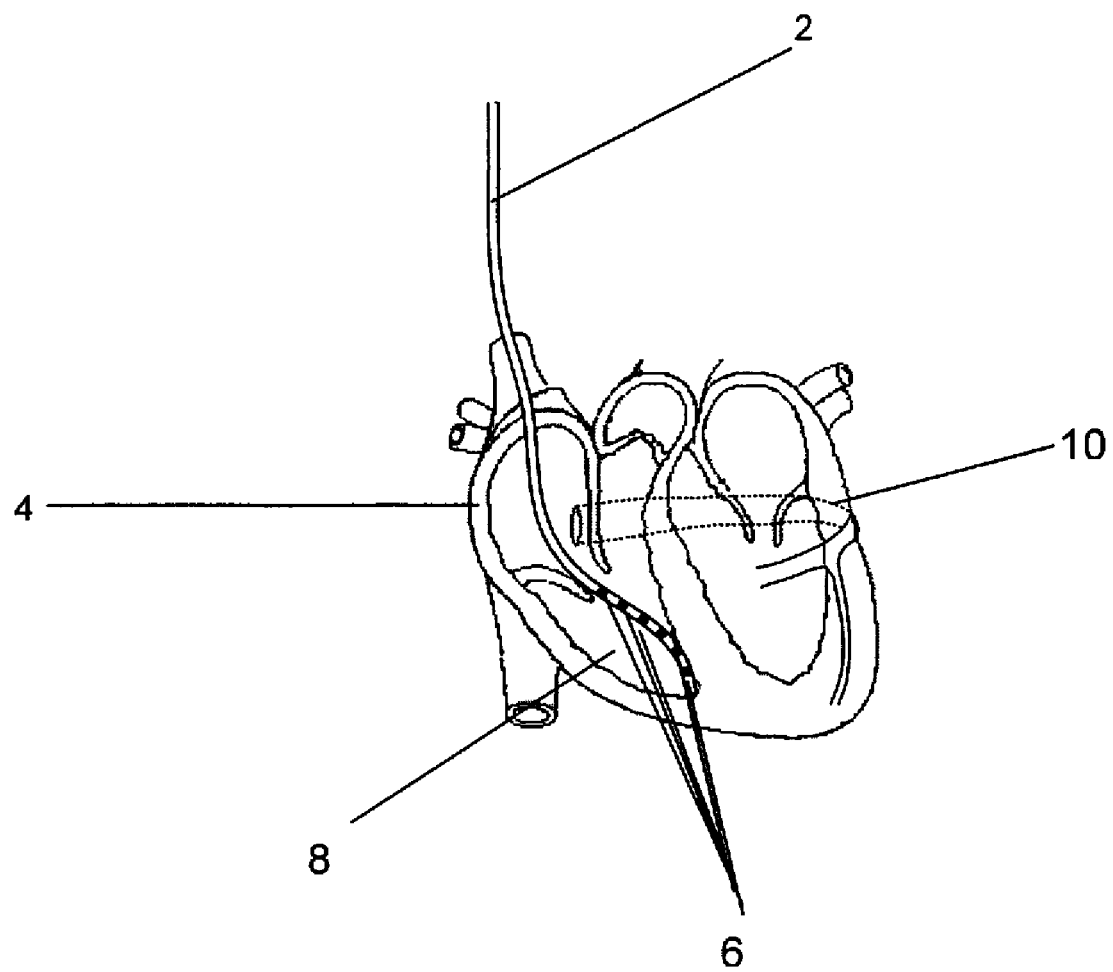
FIGS. 1, 2 and 3 respectively show different locations relative to the heart of a subject for implanting and positioning a lead, carrying multiple mechanical cardiac activity sensors along the length of the lead, in accordance with the principles of the present invention.

FIG. 1 shows a lead 2 implanted in a person's heart 4 with a plurality of sensing elements 6 located in the right ventricle 8 of the heart 4. The sensing elements 6 are distributed along a part of the lead body for sensing cardiac activity from a larger part or a larger volume of the right ventricle 8

Figure 2:
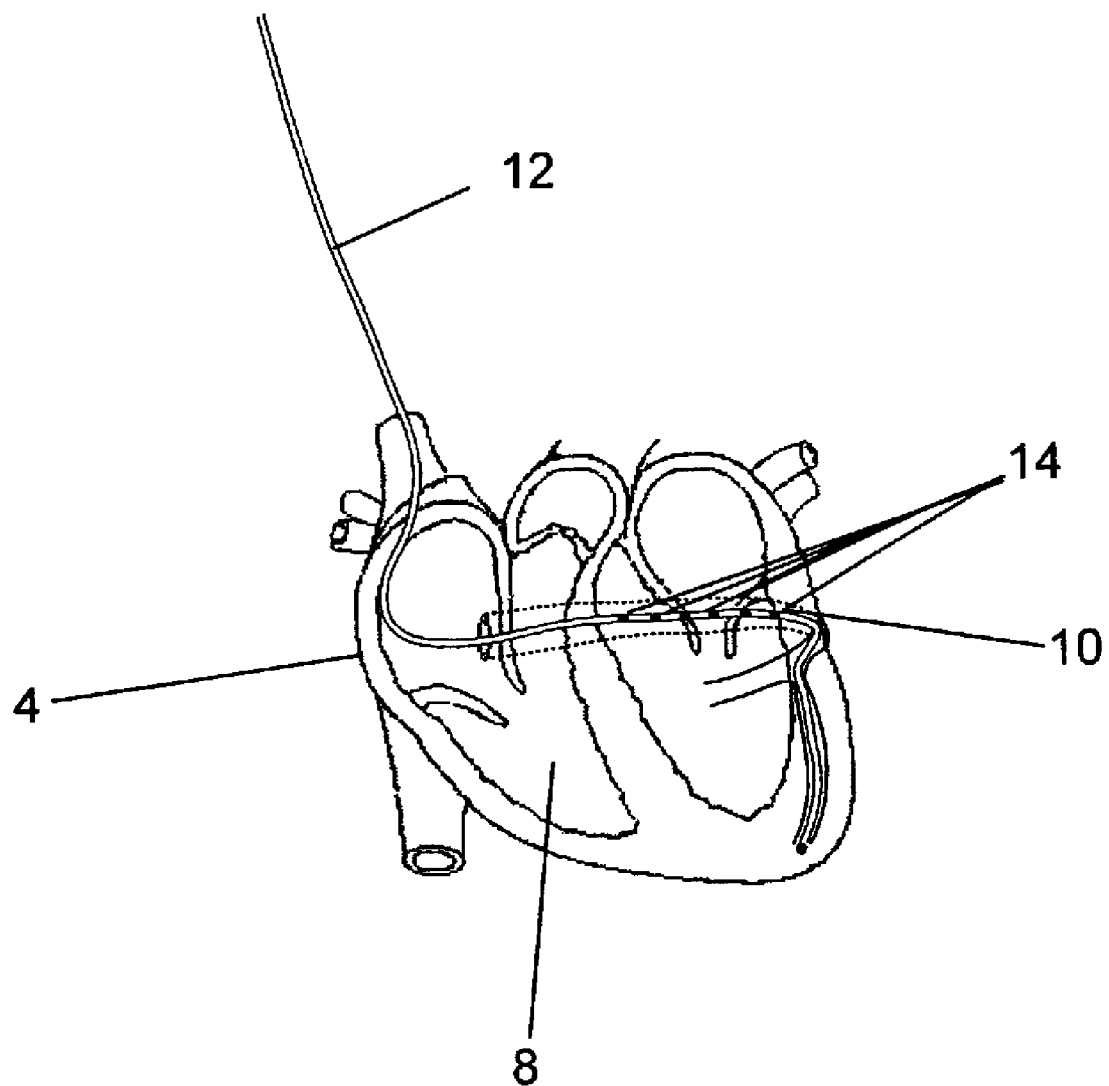
Figure 3:
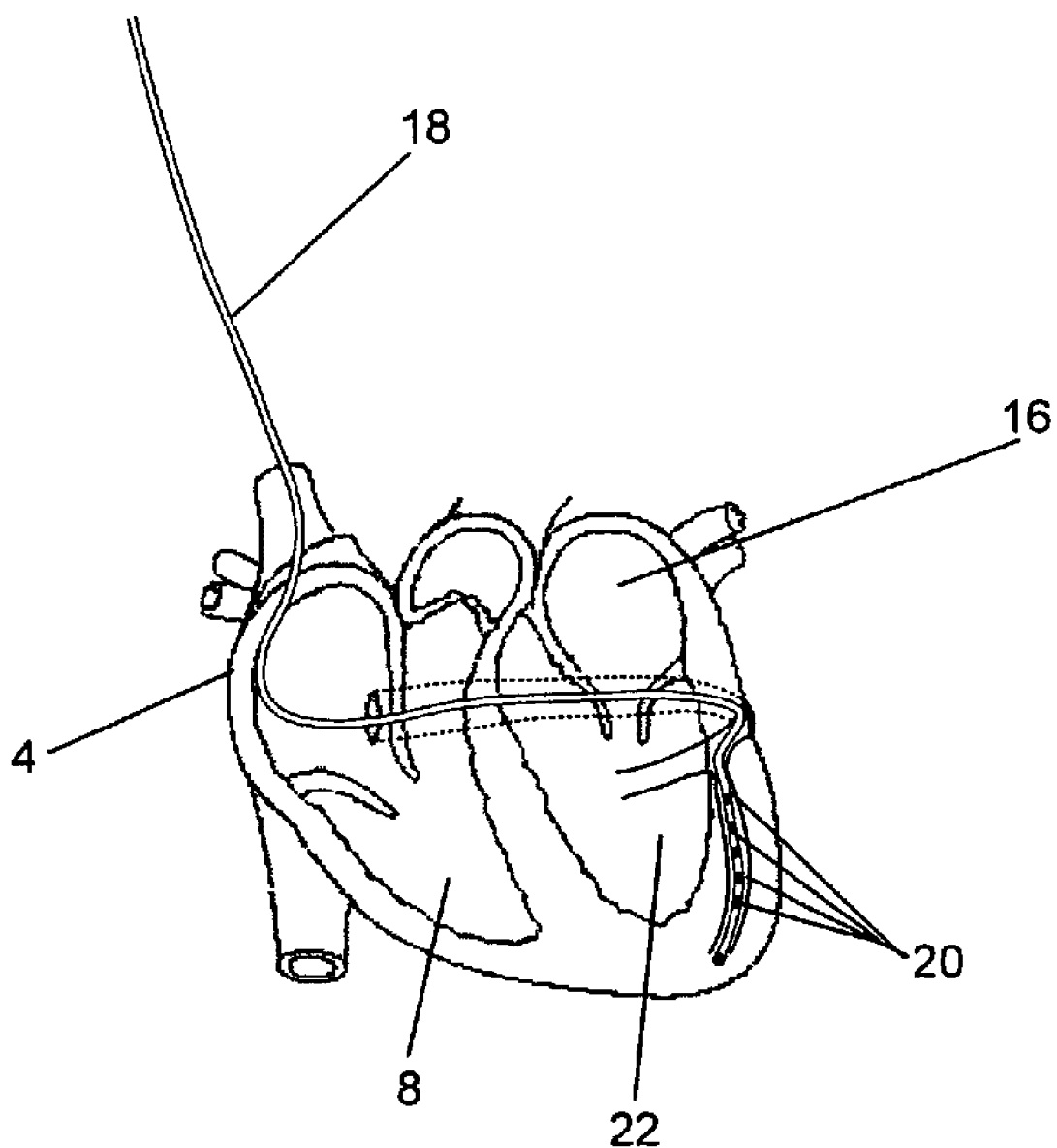

FIGS. 2 and 3 show two embodiments of the lead according to the invention implanted in a coronary vein 10 on the left side of the heart 4. The lead 12 shown in FIG. 2 is provided with a plurality of sensing elements 14 distributed along a part of the lead body adapted for implantation in the Coronary sinus for sensing the movement of the valve plane of the heart 4. The movement of the valve plane can reveal diastolic heart failure. The lead 18 shown in FIG. 3 is provided with a plurality of sensing elements 20 distributed along a part of the lead body adapted for sensing mechanical cardiac activity in the left ventricle 22 of the heart 4.

In the embodiments illustrated above the sensing elements are distributed over a length of the lead body in the range of 2-10 cm, preferably 5-10 cm.

Figure 4:
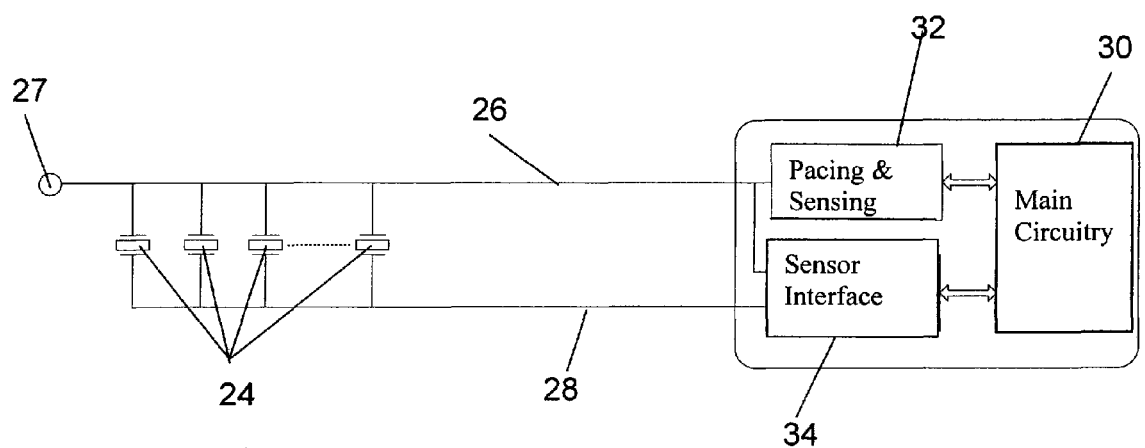
FIG. 4 is a block diagram illustrating basic circuit components of a heart stimulator according to the present invention.

FIG. 4 is a block diagram illustrating the electric circuitry of a heart stimulator to which a lead according to the invention is connected. The sensing elements 24 of the lead are electrically connected in parallel between two electric conductors 26, 28. One of the conductors 26 is intended to conduct stimulation pulses, a stimulation electrode being schematically indicated at 27, and the other conductor 28 is arranged independent of the stimulation circuitry. By this arrangement of the sensors 24, in which the polarization of each sensor 24 is of the same polarity, a sensor signal averaging is provided. By summing the signals in this way from each sensor signals in phase are added to the averaged signal, while signals out of phase will be more or less reduced. Global signals picked up from a larger volume of the heart are thus obtained on which signal local disturbances have only a minor influence.

According to an alternative embodiment each sensing element is equipped with its own conductor, or with at least one conductor of its own.

The heart simulator electric circuitry comprises, in addition to normal main circuitry 30, pacing and sensing circuitry 32 and sensor interface 34. The conductor 26 is intended to conduct stimulation pulses, whereas the conductor 28 is independent of the pacing circuitry.

The summing of the signals will be performed in a summing means of electric sensor signal processing means in the sensor interface shown in FIG. 4 or in subsequent electric circuitry.

In the above-mentioned embodiment with each sensing element having a conductor of its own the propagation in the heart of a mechanical cardiac activity, like a heart muscle contraction, a pressure pulse or blood flow along a vein, can be determined by adapting the sensor signal processing electronics to recognize electric signal patterns caused by progressive activation of the sensing elements along a lead by a propagating mechanical activity. The speed of propagation of the activity can also be calculated since the distances between the individual sensing elements along the lead are known.

Although modifications and changes may be suggested by those skilled in the art, it is the intention of the inventors to embody within the patent warranted heron all changes and modifications as reasonably and properly come within the scope of their contribution to the art.

The invention claimed is:

1. An implantable sensor lead comprising:
a lead body having a lead body length; and
a plurality of mechanical cardiac activity sensing elements distributed along a portion of said lead body length that are each configured to be in direct contact with tissue in the heart of a patient in whom the lead body is implanted and to individually detect mechanical cardiac activity of the heart of the patient in whom the lead body is implanted exclusively by interaction with said tissue due to said direct contact with said tissue, and each of said sensing elements emitting an electrical signal representing the mechanical cardiac activity directly detected thereby, said plurality of mechanical cardiac activity sensing elements, in combination, directly detecting mechanical cardiac activity of the heart of the patient over an extended region of the heart substantially corresponding to said portion of said length of said lead body.

2. An implantable sensor lead as claimed in claim 1 comprising two electrical conductors in said cardiac lead body, and wherein all of said plurality of sensing elements are electrically connected in parallel between said two conductors.

3. An implantable sensor lead as claimed in claim 1 comprising a plurality of electrical conductors in said lead body corresponding in number to said plurality of mechanical cardiac activity sensing elements, said plurality of electrical conductors being respectively connected to said plurality of mechanical cardiac activity sensing elements individually.

4. An implantable sensor lead as claimed in claim 1 wherein said lead body is configured for implantation in the right ventricle of the heart.

5. An implantable sensor lead as claimed in claim 1 wherein said lead body is configured for implantation in a coronary vein at a left side of the heart.

6. An implantable sensor lead as claimed in claim 5 wherein said lead body is configured for implantation in the coronary sinus vein.

7. An implantable sensor lead as claimed in claim 1 wherein said lead body is configured for implantation in an interventricular vein of the heart.

8. An implantable sensor lead as claimed in claim 1 wherein said plurality of sensing elements are arranged over a portion of said length of said lead body comprising 5 to 10 cm.

9. An electronic medical device comprising:
an implantable sensor lead comprising a lead body having a lead body length, and a plurality of mechanical cardiac activity sensing elements distributed along a portion of said lead body length that are each configured to be in direct contact with tissue in the heart of a patient in whom the lead body is implanted and to individually detect mechanical cardiac activity of the heart of the patient in whom the lead body is implanted exclusively by interaction with said tissue due to said direct contact with said tissue, and each of said sensing elements emitting an electrical signal representing the mechanical cardiac activity directly detected thereby, said plurality of mechanical cardiac activity sensing elements, in combination, directly detecting mechanical cardiac activity of the heart of the patient over an extended region of the heart substantially corresponding to said portion of said length of said lead body; and
a processor supplied with said signals emitted by said mechanical cardiac activity sensing elements, said processor analyzing said signals and identifying an attribute of said mechanical cardiac activity therefrom, and emitting a processor output signal indicative of said attribute.

10. A medical device as claimed in claim 9 wherein said signal processor comprises a summing unit that adds the respective signals emitted by said plurality of mechanical activity sensing elements.

11. A medical device as claimed in claim 10 wherein said processor comprises a sensor interface that interfaces said processor with said plurality of mechanical cardiac activity sensing elements, and wherein said summing unit is located in said sensor interface.

12. A medical device as claimed in claim 11 wherein said processor is configured to identify an electrical signal pattern caused by progressive emission of respective signals by the respective cardiac activity sensing elements.

13. An implantable cardiac stimulator comprising:
a pulse generator configured to deliver electrical stimulation pulses to the heart of a patient;
an implantable sensor lead comprising a lead body having a lead body length, and a plurality of mechanical cardiac activity sensing elements distributed along a portion of said lead body length that are each configured to be in direct contact with tissue in the heart of a patient in whom the lead body is implanted and to individually detect mechanical cardiac activity of the heart of the patient in whom the lead body is implanted exclusively by interaction with said tissue due to said direct contact with said tissue, and each of said sensing elements emitting an electrical signal representing the mechanical cardiac activity directly detected thereby, said plurality of mechanical cardiac activity sensing elements, in combination, directly detecting mechanical cardiac activity of the heart of the patient over an extended region of the heart substantially corresponding to said portion of said length of said lead body;

a processor supplied with said signals emitted by said mechanical cardiac activity sensing elements, said processor analyzing said signals and identifying an attribute of said mechanical cardiac activity therefrom, and emitting a processor output signal indicative of said attribute; and said processor being configured to control said stimulation pulse generator dependent on the detected and analyzed mechanical cardiac activity.

14. An implantable cardiac stimulator as claimed in claim 13 wherein said lead body comprises two conductors therein, with said plurality of mechanical cardiac activity sensing elements being electrically connected in parallel between said two conductors, and wherein one of said conductors is connected to said stimulation pulse generator to conduct stimulation pulses emitted by said stimulation pulse generator, and the other of said two conductors is independent of said stimulation pulse generator.

15. A method for sensing mechanical cardiac activity of a heart comprising the steps of:

implanting a sensor lead, comprising a lead body having a length with a plurality of cardiac activity sensing elements distributed along a portion of said length, in the heart of a patient to place each of said sensing elements indirect contact with tissue in the heart;

with each of said sensing elements, detecting mechanical cardiac activity of the heart exclusively by interaction with said tissue due to said direct contact with said tissue; and from each of said sensing elements, emitting an electrical signal representing the mechanical cardiac activity directly detected thereby to produce a collection of respective electrical signals from said sensing elements that, in combination, represent the directly detected mechanical activity of the heart over an extended region of the heart, substantially corresponding to said portion of said length.

16. A method as claimed in claim 15 comprising sensing said mechanical cardiac activity individually with respective mechanical cardiac activity sensing elements in said plurality of mechanical cardiac activity sensing elements.

17. A method as claimed in claim 15 comprising summing respective electric signals from said plurality of mechanical cardiac activity sensing elements.

18. A method as claimed in claim 15 comprising automatically electronically analyzing respective electrical signals from said plurality of mechanical cardiac activity sensing elements to identify a pattern representing propagation of said mechanical cardiac activity in the heart.

19. A method as claimed in claim 15 comprising implanting said lead body in the right ventricle of the heart, and sensing said mechanical cardiac activity over an extended region of said right ventricle.

20. A method as claimed in claim 15 comprising implanting said lead body in a coronary vein at a left side of the heart, and sensing said mechanical cardiac activity over an extended region surrounding the coronary vein.

21. A method as claimed in claim 20 comprising implanting said lead body in the coronary sinus vein, and automatically electronically analyzing mechanical cardiac activity detected by said plurality of mechanical cardiac activity sensing elements to identify movement of the valve plane of the heart.

22. A method as claimed in claim 15 comprising implanting said lead body in an interventricular vein of the heart, and sensing said mechanical cardiac activity in an extended region surrounding said interventricular vein.

23. A method as claimed in claim 15 comprising distributing said plurality of mechanical cardiac activity sensing elements along said portion of said length comprising 5 to 10 cm.

* * * * *